United States Patent [19]

Schmid et al.

[11] Patent Number: 5,401,306
[45] Date of Patent: Mar. 28, 1995

[54] LUSTER PIGMENTS WITH A METAL SULFIDE COATING

[75] Inventors: Raimund Schmid, Neustadt; Norbert Mronga, Dossenheim, both of Germany

[73] Assignee: BASF Aktiengesellschaft, Ludwigshafen, Germany

[21] Appl. No.: 287,403

[22] Filed: Aug. 5, 1994

Related U.S. Application Data

[63] Continuation of Ser. No. 92,497, Jul. 16, 1993.

[30] Foreign Application Priority Data

Jul. 16, 1992 [DE] Germany ............ 42 23 383.6

[51] Int. Cl.$^6$ ............ C04B 14/20; C04B 14/00
[52] U.S. Cl. ............ 106/417; 106/404; 106/420; 106/439; 106/441; 106/479
[58] Field of Search ............ 106/417, 404, 420, 439, 106/440, 441, 479, 480

[56] References Cited

U.S. PATENT DOCUMENTS

| | | | |
|---|---|---|---|
| 2,995,459 | 8/1961 | Soloway | 106/417 |
| 3,087,828 | 4/1963 | Linton | 106/417 |
| 3,123,490 | 3/1964 | Bolomey | 106/415 |
| 3,374,105 | 3/1968 | Bolomey | 106/420 X |
| 4,086,100 | 4/1978 | Esselborn et al. | 106/417 |
| 4,328,042 | 5/1981 | Ostertag et al. | 106/415 |
| 4,365,374 | 12/1981 | Bennett | 14/71.7 |
| 4,552,593 | 11/1985 | Ostertag | 106/417 |
| 4,618,375 | 10/1986 | Patil et al. | 106/404 |
| 5,034,430 | 7/1991 | Babler | 106/479 |
| 5,063,258 | 11/1991 | Babler | 523/171 |
| 5,091,010 | 2/1992 | Souma et al. | 106/404 |

FOREIGN PATENT DOCUMENTS 0360740  3/1990  European Pat. Off. .
2134538  12/1972  France .

*Primary Examiner*—Helene Klemanski
*Attorney, Agent, or Firm*—Oblon, Spivak, McClelland, Maier & Neustadt

[57] ABSTRACT

Luster pigments based on coated, plateletlike, silicatic or metallic substrates wherein the coating comprises a metal sulfide are useful for coloring paints, printing inks, plastics, glasses, ceramic products and decorative cosmetic preparations.

10 Claims, No Drawings

LUSTER PIGMENTS WITH A METAL SULFIDE COATING

This application is a Continuation of application Ser. No. 08/092,497, filed on Jul. 16, 1993, now abandoned.

The present invention relates to novel luster pigments based on coated, plateletlike, silicatic or metallic substrates where the coating comprises a metal sulfide.

The invention further relates to the preparation of these luster pigments and to the use thereof for coloring paints, printing inks, plastics, glasses, ceramic products and decorative cosmetic preparations.

Luster or effect pigments are increasingly used in many sectors of industry, for example in automotive coatings, decorative coatings, plastics pigmentation, printing inks, in particular encaustic inks, paints and cosmetics.

Their optical effect is based on directional reflection at predominantly sheetlike, oriented metallic or strongly refractive pigment particles. According to the nature of the pigment particles, the pigments are also known as metallic effect pigments (eg. aluminum, zinc, copper or alloys thereof) or pearl luster pigments (eg. based on titanium dioxide-coated mica such as muscovite, phlogopite and biotite, talc or glass).

Luster pigments may have a multiphase structure, formed by coating the starting substrates with thin films of highly refractive oxides such as chromium(III) oxide, in particular iron oxide and titanium oxide. Interference with or without absorption will in these cases result in a multiplicity of hue variations depending on the thickness of the oxide layer; these pigments are also known as interference pigments or, in the case of a metallic substrate, as interference-reflection pigments.

As a result of the incident light being reflected directionally at the plateletlike pigment particles, coated luster pigments that are oriented, for example in a lacquer, exhibit goniochromaticity; that is, their perceived color (lightness and/or hue and/or chroma) varies with the angle of illumination or observation. These effects can be ascribed to a complex interplay of reflection and transmission of the incident light, the color of which can be affected by phenomena due to the pigment particles, such as interference in thin films and absorption by colored centers.

U.S. Pat. No. 2,995,459 discloses the preparation of luster pigments by coating the costly, plateletlike materials guanine, lead carbonate and bismuth oxychloride with cadmium sulfide, tin sulfide, iron sulfide, manganese sulfide or antimony sulfide. U.S. Pat. No. 3,123,490 describes the use of zinc sulfide for preparing luster pigments which, however, distinctly differ from the pigments of the invention in structure.

Metal sulfides which crystallize in platelet form such as the highly refractive and reflective molybdenum sulfide ($MoS_2$) can also be used directly as single-phase luster pigments. Although these pigments can be used to produce luster effects, without the additional use of further colorants such as pearl luster pigments or organic pigments the range of hues is limited to dark blue or black (U.S. Pat. No. 5,063,258 or EP-A-360 740).

It is an object of the present invention to make available novel luster pigments which are free of the disadvantages mentioned and which shall have altogether advantageous application properties.

We have found that this object is achieved by luster pigments based on coated, plateletlike, silicatic or metallic substrates where the coating comprises a metal sulfide.

We have also found a process for preparing these luster pigments, which comprises coating the substrate, which may if desired have already been coated with a metal oxide, with a) a metal or metal oxide layer produced in a conventional manner by gas phase decomposition of volatile metal compounds in the presence of an inert gas or of oxygen and/or water vapor and thereafter converted by reaction with a volatile, sulfur-containing compound or sulfur vapor into the desired coating that comprises metal sulfide, or b) directly with a coating comprising metal sulfide by gas phase decomposition of volatile metal compounds in the presence of volatile, sulfur-containing compound or sulfur vapor, and if desired then coating the substrate thus coated with a further metal oxide layer in a conventional manner.

We have additionally found that these luster pigments are useful for coloring paints, printing inks, plastics, glasses, ceramic products and decorative cosmetic preparations.

Suitable substrates for the luster pigments of the invention are in particular silicated or metallic platelets or mixtures thereof.

Particular preference is given to light-colored or white mica, in particular flakes of wet ground muscovite. It is of course also possible to use other natural micas such as phlogopite, biotite, artificial mica and talc and glass flakes.

Suitable metallic substrates for the pigments of the invention are all metals in platelet form known for metallic effect pigments; examples besides copper and its alloys such as brass or bronzes are in particular aluminum and its alloys such as aluminum bronze. Preference is given to aluminum platelets which are producible in a simple manner by stamping out of aluminum foil or by conventional atomization or grinding techniques. It is also possible to use commercial products, in which case the metal surface should be substantially free of fats or other coating media.

The substrate particles used may already be coated with a layer of highly refractive, colorless or colored metal oxide. This is advantageous in particular when the pigments to be obtained are to show chromatic, ie. non-black, interference colors. It is possible to use the usual oxides used for coating luster pigments such as silicon oxide, tin oxide, bismuth oxide, zinc oxide, aluminum oxide and chromium oxide and in particular iron dioxide and zirconium dioxide and especially titanium dioxide.

Metal oxide-coated silicatic and metallic pigments are generally known and in the case of coated mica pigments also commercially obtainable under the names Iriodin ® (E. Merck, Darmstadt), Flonac ® (Kemira Oy, Pori, Finland) and Mearlin ® (Mearl Corporation, New York). Metal oxide-coated mica pigments are known to be preparable from an aqueous phase (DE-A-14 67 468, DE-A-25 22 572) or from the gas phase (EP-A-45 581, DE-A-32 37 264), and the corresponding metal pigments can likewise be prepared by coating from the gas phase (EP-A-33 457) or from an alcoholic solution (DE-A-35 34 477, EP-A-328 906).

The size of the substrate particles is not critical per se and can be adapted to the particular application. In general, the particles have largest diameters of about 1–200 μm, in particular about 5–100 μm, and thicknesses of in general about 0.1–5 μm, in particular about 0.5 μm.

If the substrate particles have a first coating with metal oxide, the thickness of this layer will in general be within the range known for conventional pearl luster pigments of about 20–400 nm, preferably 35–250 nm.

The essential feature of the luster pigments of the invention is the metal sulfide layer, which is applied either directly to the uncoated or to the metal oxide-coated substrate particles.

Suitable for forming this layer are in particular the non-selectively absorbing sulfides of cobalt and nickel, in particular of iron, chromium and tungsten and very particularly of molybdenum. These sulfides can be present individually or else in the form of mixtures, eg. $MoS_2/WS_2$. It is also possible to use mixtures with the corresponding oxides, eg. mixtures of lower molybdenum oxides and molybdenum sulfide, or the corresponding metals, which can be of advantage for the coloristic properties of the pigment.

The metal sulfide-containing layer can advantageously be applied from the gas phase by the below-described process of the invention.

The sulfide-containing layers thus obtainable are notable for a uniform, homogeneous, filmlike structure. Depending on their thickness they transmit light to a certain degree and contribute to interference.

Semi-transparent sulfidic layers which in general have a thickness of from 0.1 to 50 nm, preferably <20 nm, reduce the white content of the incident and reflected light and, if the substrate already has a metal oxide coating, in this way bring about an enhancement of and, depending on their thickness, also a change in the interference color of the substrate.

A particularly pronounced shift in hue can be observed with $MoS_2$ layers. It is due to the high refractive index of the $MoS_2$, $n=5.6$ ($\lambda=500$ nm), which is reflected in the optical layer thickness defined by the product of refractive index and geometrical layer thickness.

$MoS_2$-coated interference-reflection pigments which are particularly brilliant and strong in color are obtained in the blue region. For example, a titanium dioxide-coated aluminum pigment having a delicate blue interference color can be converted with a coating of $MoS_2$ into a pigment with a deep cornflower blue color.

Opaque sulfidic layers are generally the result of layer thicknesses >100 nm. In these cases, whether the substrate is coated with sulfide only or with oxide and sulfide, the luster pigments obtained are black and have a very smooth surface owing to the high quality of the sulfide layer applied according to the invention.

Almost opaque sulfidic layers generally about 20–80 nm in thickness give rise in the case of interference-capable, ie. already metal oxide-coated, substrates to almost black luster pigments where the interference color of the multi-layer system still shines through weakly at the luster angle. This effect, albeit to a minor extent, can be observed in pigments coated with only one transparent metal sulfide-containing layer. This kind of pigment is particularly attractive for automotive coatings having muted hues.

When comprising a still transparent sulfide-containing layer on interference-capable material, the luster pigments of the invention thus exhibit useful, angle-dependent color and lightness sensations in the applied state. The angle Of observation dictates whether the interference color of the multi-layer system or the black color of the non-selectively absorbing, sulfide-containing layer is seen.

If the metal sulfide layer consists essentially of $MoS_2$, then the pigments of the invention show not only the color effects mentioned but also electrical conductivity of the order of that of the semiconductors, which increases on exposure of the pigments to light. These pigments also show useful reflectivity and absorptivity in the infrared region.

The metal sulfides used according to the invention and hence the pigments coated with them too are notable not least for their chemical resistance, for example to acids and bases, and for their low solubility in water. $MoS_2$ moreover is very stable to heat.

Furthermore, it can be of advantage for the luster pigments of the invention to be coated additionally with a top coat comprising a colorless or selectively absorbing metal oxide. In this case the sulfide-containing layers are preferably thin layers about 2–30 nm in thickness. This top layer can have the purpose of protecting the sulfide layer in certain applications. It also results in pigments having particularly high hiding power. If colored oxides are used in the top layer, the color flop will be from the respective interference color to the intrinsic color of the oxide, in the case of iron(III) oxide for example to reddish brown. In general, the thin oxide layers contribute to the interference of the pigment, continuing the interference chain in the area determined by the starting material. This additional coating thus advantageously widens the color palette of the luster pigments.

The oxidic top layer can be composed of the usual highly refractive, colorless and colored but not black metal oxides suitable for coating interference pigments. Examples are titanium oxide, zirconium oxide, tin oxide, chromium oxide, iron oxide, aluminum oxide, silicon oxide and zinc oxide and mixtures thereof. Particular preference is given to iron(III) oxide, titanium dioxide, zirconium dioxide and mixtures thereof.

The thickness of the third layer is not critical per se and in general will be about 1–400 nm, in particular 5–200 nm.

Advantageously it is likewise deposited from the gas phase.

In the novel process for preparing the novel luster pigments, the metal sulfide-containing layer is applied to the substrate, which may already have a first coating of metal oxide, from the gas phase.

The process of the invention can be carried out in two different versions. In version a), initially a metal or metal oxide layer is deposited on the substrate in a conventional manner by gas phase decomposition of volatile compounds of the metals and this metal or metal oxide layer is then converted into the desired sulfide layer by reaction with suitable sulfur-containing compounds or sulfur vapor. In version b), an appropriate metal compound is decomposed in the presence of the sulfur-donating compound or of the sulfur vapor and directly deposited as the sulfide. In general, version a) will be preferable, since in version b) it will in general be necessary to free larger gas quantities of converted or unconverted sulfur compound.

The process of the invention can advantageously be carried out in a heatable fluidized-bed reactor as described for example in EP-A-45 581, in which initially the substrate-particles are fluidized by a gas and heated to the decomposition temperature of the respective metal compound, in general to 70°–350° C. The vaporized metal compounds and the gases required for decomposition or further reaction are then introduced via separate nozzles.

The preferred volatile metal compounds not only for version a) but also for version b) are the carbonyls, ie. in particular iron pentacarbonyl, chromium hexacarbonyl, molybdenum hexacarbonyl and tungsten hexacarbonyl, as well as nickel tetracarbonyl and dimeric cobalt tetracarbonyl.

If metallic layers are to be deposited in version a), the carbonyls are decomposed in the presence of an inert gas such as nitrogen or argon as described in the earlier German Patent Application P 4141069.6.

If metal oxide layers are to be applied initially, not only the usual oxides are suitable such as $Fe_2O_3$, $Cr_2O_3$, $MoO_3$, $WO_3$, NiO and CoO but also lower oxides such as $Fe_3O_4$ and in particular molybdenum and tungsten suboxides.

The deposition of the customary metal oxides can take place as described for example in EP-A-45 581 in the presence of oxygen (or air) with or without water vapor. Furthermore, it is also possible to deposit metal layers (eg. Mo) initially and then to convert them, for example with air, at temperatures of in general 300°–400° C. into oxide layers (eg. $MoO_3$).

To produce an $Fe_3O_4$ layer, the iron carbonyl is hydrolyzed with water vapor in the absence of oxygen (see likewise P 4141069.6).

Molybdenum or tungsten suboxide layers can be obtained as described in the earlier German Application P 4221010.0 by decomposing the carbonyls with oxygen or air/nitrogen mixtures in the presence or absence of water vapor. For this the oxygen should in general account for 0.5–10% by volume, preferably 0.8–6% by volume, of the total amount of gas in the reactor and the water vapor for about 0–2% by volume. The necessary reaction temperature is in general 150°–250° C., preferably 200°–220° C.

As is generally customary for chemical vapor deposition (CVD) in a fluidized bed reactor, the metal carbonyls are advantageously vaporized in a vaporizer upstream of the reactor, transported into the reactor with an inert carrier gas, preferably nitrogen, and decomposed in the reactor by reaction gases (oxygen or air and/or water vapor) mixed in with the fluidizing gas.

To obtain homogeneous layers that enrobe the substrate uniformly and completely, the gas quantity of the metal carbonyl should in general not be more than 5% by volume, preferably not more than 2% by volume, of the total quantity of gas in the reactor.

The metal or metal oxide layers obtained in version a) can be converted into the desired sulfidic layers in the same reactor without intermediate isolation using an inert fluidizing gas (preferably nitrogen) admixed with the volatile sulfur-containing compound or the sulfur vapor. However, this reaction can also be carried out in other apparatus such as gastight tubular or chamber furnaces after intermediate isolation of the coated substrate.

Similarly, in version b) the metal carbonyl used is decomposed in the presence of the sulfur-donating compound or of the sulfur vapor and an inert fluidizing gas. The concentration of the gaseous sulfur-containing compound or of the sulfur vapor should be not more than 5% by volume, preferably 2–4% by volume.

Suitable sulfur-containing compounds for both versions include not only $C_1$–$C_5$-thioalcohols and $C_2$–$C_4$-thioethers, such as methyl, ethyl, propyl, butyl or pentylmercaptan, dimethylsulfide and diethylsufide, carbon disulfide and elemental sulfur but in particular hydrogen sulfide.

The reaction temperatures range in general from 200° to 500° C., preferably from 300° to 400° C.

After the coating with the sulfide-containing layer has been completed, it is advisable to purge the reactor for about a further 1–2 h with nitrogen to remove residual quantities of hydrogen sulfide and/or the other sulfur compounds. Excess hydrogen sulfide or sulfur or sulfur dioxide formed in the course of the reaction can then be removed in a simple manner from the waste gas by washing with sodium hydroxide solution.

If desired, the sulfide-coated substrate particles can be additionally coated in a conventional manner with an oxidic top layer. This can be of advantage to improve the light or weathering fastness.

Suitable starting compounds in addition to the carbonyls are the halides, in particular chlorides, both aromatic alkoxides such as phenoxides and benzyl alkoxides and aliphatic alkoxides, in particular $C_1$–$C_4$-alkoxides such as n-, iso- and tert-butoxides, preferably methoxides and ethoxides and particularly preferably n- and iso-propoxides. The halides and alkoxides are hydrolyzed by water vapor as described in the earlier German Patent Application P 4217511.9, where oxygen (air) may be present in the case of halides. Examples of preferred compounds are iron pentacarbonyl, chromium hexacarbonyl, aluminum chloride, silicon tetrachloride, tin tetrachloride, titanium tetrachloride, zirconium tetrachloride, titanium n-propoxide, titanium isopropoxide, zirconium n-propoxide, and zirconium isopropoxide.

The decomposition of these metal compounds is advantageously carried out at <250° C., in particular at from 100° to 200° C. Which metal compound is best used depends on the sulfide layer applied. If the sulfide-containing layers are under these conditions sensitive to oxidation, it is preferable to use for example an alkoxide.

The process of the invention makes it possible to incorporate sulfide-containing, highly refractive, strongly absorbing layers into multi-phase pigments and hence the reproducible production of high quality luster pigments particularly notable for their homogeneous, uniform layers enrobing the substrate particles in film fashion.

The novel luster pigments are advantageous for many purposes, such as the coloring of paints, printing inks, plastics, glasses, ceramic products and decorative cosmetic preparations. The strongly angle-dependent color flop of the novel interference-capable pigments in the application state makes it possible to manufacture encaustic and special effect inks, in particular for securities printing and for preparing forgeryproof documents. The high acid and alkali resistance of $MoS_2$ is also of particular interest in this context. Owing to their high hiding power and their attractive color characteristics, the molybdenum or iron sulfide-coated pigments are suitable in particular for automotive coating, since if they are used it is possible to dispense with the use of the otherwise necessary base coating and other colorants. In addition, the favorable surface properties of $MoS_2$-coated luster pigments ($MoS_2$ itself is frequently used as lubricant) facilitate their incorporation into the application media.

EXAMPLES

Preparation of luster pigments according to the invention

The exemplified coatings with a metal or a metal oxide of mica pigments with or without a coating of $TiO_2$ and of aluminum pigments were each carried out in an externally heatable fluidized bed reactor made of glass, having a diameter of 8 cm and a height of 80 cm, and equipped with a glass frit bottom and filter socks, suspended from the top and to be cleaned with a nitrogen jet, and two gas injection nozzles situated on the side above the frit bottom.

The conversion of the metal or metal oxide layer into the desired sulfide layer was carried out in a rotary sphere oven apparatus, consisting essentially of a mechanically rotatable round-bottom quartz flask heatable by a clamshell oven and having gas inlet and outlet lines in the axis of rotation (Examples 1 to 7), or in a fluidized bed reactor (Examples 8 and 9).

A) Preparation of metal sulfide-coated mica pigments

EXAMPLES 1 TO 4

200 g of the mica pigment (crude mica or $TiO_2$-coated mica) specified in Table 1 were heated to 220° C. in the fluidized bed reactor under fluidization with nitrogen at a total rate of 800 l/h, half of the nitrogen being passed through a 70° C. reservoir of molybdenum hexacarbonyl. In this way ×g of $Mo(CO)_6$ were introduced over 8 h and deposited on the substrate as a hydrolysis-sensitive molybdenum film.

50 g of the black molybdenum-coated pigment were heated to 300° C. in the rotary sphere oven under an air stream to oxidize the molybdenum to the colorless molybdenum trioxide. After blanketing with nitrogen for 2 hours 6 l of hydrogen sulfide were passed through at 400°–450° C. at a rate of 2 l/h, converting the $MoO_3$ into the black molybdenum sulfide $MoS_2$ with additional formation of water vapor and sulfur. The sulfur formed sublimed out and was collected in colloid form in 10% strength by weight sodium hydroxide solution.

After the reaction had ended, the product was cooled down to room temperature over 3 h under a blanket of inert gas.

The molybdenum sulfide-coated pigments thus obtained showed strong luster, excellent hiding power and no sensitivity to water.

Further details of these experiments and the results thereof are summarized in the table below.

C. and with the addition of 76.9 g of $Mo(CO)_6$. The pigment obtained exhibited a color flop from blue to green.

50 g of this pigment were reacted with hydrogen sulfide as described in Example 1 to form a black molybdenum sulfide-coated pigment (9.0% by weight of Mo, 4.7% by weight of S).

Applied in a lacquer, the black pigment showed the green interference color weakly at a certain angle of observation.

The pigment did not undergo any changes in boiling water or in 80° C. hydrochloric acid (pH 1).

EXAMPLE 6

In a somewhat larger, but otherwise identical fluidized bed reactor, 800 g of the $TiO_2$-coated mica pigment Iriodin 9103 Sterling Silver WR were heated to 180° C. under fluidization with a total of 2000 l/h of nitrogen, of which one fifth passed through an iron pentacarbonyl reservoir temperature controlled to 35° C. In this way 870 g of $Fe(CO)_5$ were introduced. At the same time air for the oxidation (to form $Fe_2O_3$) was passed in at a rate of 600 l/h via a water reservoir temperature controlled to 50° C.

50 g of the brownish red, $Fe_2O_3$-coated pigment were reacted with hydrogen sulfide as described in Example 1 to form a black, iron sulfide-coated pigment (17.9% by weight of Fe, 11.4% by weight of S), which, applied in a lacquer, showed a weak golden luster at a certain angle of observation.

EXAMPLE 7

200 g of the $TiO_2$-coated mica pigment Iriodin 9225 rutile Pearl Blue WR were heated to 220° C. under fluidization with a total of 800 l/h of nitrogen, of which half passed through a reservoir of 60.0 g of iron pentacarbonyl temperature controlled to 35° C. To achieve surface passivation of the iron layer deposited on the substrate particles, cooling down to 100° C. was followed by the introduction of 25 l of air over 30 min.

50 g of this pigment were reacted with hydrogen sulfide as described in Example 1 to form a deep blue iron sulfide-coated pigment (7.4% by weight of Fe, 7.1% by weight of S).

B) Preparation of metal sulfide-coated aluminum pigments

EXAMPLE 8

A mixture of 100 g of an aluminum powder with an

TABLE

| Ex. | Mica pigment | × g of $Mo(CO)_6$ | Mo content [% by weight] | S content [% by weight] | Hue or color flop |
| --- | --- | --- | --- | --- | --- |
| 1 | Wet ground muscovite, particle size <100 μM | 43.6 | 3.9 | 2.0 | grayish black |
| 2 | Iriodin ® 9205 rutile Brilliant Yellow WR (Merck) | 20.2 | 3.2 | 2.2 | copper |
| 3 | Iriodin 9225 rutile Pearl Blue WR | 40.8 | 5.7 | 4.1 | black → greenish blue |
| 4 | Iriodin 9215 rutile Pearl Red WR | 50.3 | 7.8 | 6.2 | black → pale green |

EXAMPLE 5

200 g of the $TiO_2$-coated mica pigment Iriodin 9235 rutile Pearl Green WR were coated with blue molybdenum suboxide as described in Example 1, but with the additional introduction of 50 l/h of air having passed through a water reservoir temperature controlled to 50° average particle diameter of 20 μm and a BET surface area of 4.5 $m^2/g$ and 100 g of a coarser aluminum powder (average particle diameter 60 μm, BET surface area 1.5 $m^2/g$) was heated to 220° C. under fluidization with nitrogen at a total gas rate of 800 l/h, half of the nitrogen passing through a reservoir of molybdenum hexacarbonyl temperature controlled to 70° C. In this way 81.7 g of Mo(CO)$_6$ were introduced over 10 h and by the simultaneous addition of 200 l/h of air oxidized to molybdenum trioxide, which became deposited as a film on the substrate.

Then the air supply was stopped, followed after a further 30 min by the nitrogen supply. After the temperature was increased to 300° C. a mixture of 1 l/h of hydrogen sulfide and 4 l/h of nitrogen was passed in over 10 h.

The pigment obtained was black and had a weakly golden interference color (19.0% by weight of Mo, 17.8% by weight of S).

EXAMPLE 9

200 g of the aluminum mixture of Example 8 were heated to 180° C. under fluidization with nitrogen at a total gas rate of 800 l/h, half of the nitrogen passing through a titanium tetrachloride reservoir temperature controlled to 35° C. and half through a water reservoir temperature controlled to 35° C. In this way 65.0 g of TiCl$_4$ were introduced over 10 h and became deposited as a titanium dioxide film on the aluminum particles.

On completion of the deposition of the TiO$_2$, the reactor temperature was raised to 220° C. Then 400 l/h of nitrogen were passed through a reservoir of molybdenum hexacarbonyl heated to 80° C. In this way 81.7 g of Mo(CO)$_6$ were introduced and, by the simultaneous addition of 50 l/h of air, became oxidized to molybdenum suboxide which formed a film on the substrate.

Then the molybdenum-coated blue pigment was reacted with hydrogen sulfide as described in Example 8 to form a deeply cornflower-blue metallic pigment (8.9% by weight of Mo, 1.9% by weight of S).

We claim:

1. Luster pigments based on coated platelet shaped, silicatic or metallic substrates wherein the coating comprises a non-selectively absorbing, black metal sulfide selected from the group consisting of a sulfide of chromium, tungsten and molybdenum.

2. Luster pigments as claimed in claim 1 comprising
A) a first metal sulfide-containing layer and
B) optionally a second layer comprising a metal oxide.

3. Luster pigments as claimed in claim 1 comprising
A) a first layer comprising a metal oxide,
B) a second layer comprising a metal sulfide, and
C) optionally a third layer comprising a metal oxide.

4. Luster pigments as claimed in claim 1 wherein the metal sulfide-containing layer comprises a metal sulfide or a mixture of various metal sulfides or a mixture of metal sulfide and the respective metal oxide or a mixture of a metal sulfide and the respective metal.

5. Luster pigments as claimed in claim 1 wherein the coating further comprises titanium oxide, zirconium oxide, tin oxide, iron oxide, chromium oxide, vanadium oxide, cobalt oxide and/or nickel oxide.

6. A process for preparing the luster pigments of claim 1, which comprises coating the substrate, which may optionally have already been coated with a metal oxide, with
a) a metal or metal oxide layer by gas phase decomposition of volatile metal compounds in the presence of an inert gas or of oxygen and/or water vapor and thereafter converted by reaction with a volatile, sulfur-containing compound or sulfur vapor into the metal sulfide coating, or
b) directly with a coating comprising metal sulfide by gas phase decomposition of volatile metal compounds in the presence of volatile, sulfur-containing compound or sulfur vapor,
and optionally then coating the substrate thus coated with a further metal oxide layer.

7. A process as claimed in claim 6, wherein the volatile, sulfur-containing compound used is hydrogen sulfide, carbon disulfide, a $C_1$–$C_5$-thioalcohol or a $C_2$–$C_4$-thioether.

8. A process as claimed in claim 6, wherein the volatile metal compound used is a carbonyl.

9. A method of coloring paints, printing inks, plastics, glasses, ceramic products and decorative cosmetic preparations, which comprises using the luster pigments of claim 1.

10. Luster pigments as claimed in claim 1, wherein the black metal sulfide is a sulfide of molybdenum.

* * * * *